United States Patent [19]

Duemmen

[11] Patent Number: Plant 7,356

[45] Date of Patent: Oct. 16, 1990

[54] GERANIUM PLANT NAMED 'DUEGE'

[76] Inventor: Guenter Duemmen, Dammweg 18-20, D-4134 Rheinberg 4, Fed. Rep. of Germany

[21] Appl. No.: 196,282

[22] Filed: May 20, 1988

[51] Int. Cl.[5] ..... A01H 5/00

[52] U.S. Cl. ..... Plt./68

[58] Field of Search ..... Plt./68

[56] References Cited

U.S. PATENT DOCUMENTS

P.P. 6,708 3/1989 Duemmen ..... Plt. 68

*Primary Examiner*—James R. Feyrer

*Attorney, Agent, or Firm*—Marks Murase & White

[57] ABSTRACT

A new and distinct Geranium plant known by the cultivar name Duege is characterized by a new color, a great number of umbels, a semi-double flower form, and very early flowering.

1 Drawing Sheet

BACKGROUND OF THE NEW PLANT

The present invention comprises a new and distinct cultivar of Geranium, botanically known as *Pelargonium zonale,* and hereinafter referred to by the cultivar name Duege.

Duege is a product of planned breeding program which had the objective of creating new Geranium cultivars with pale red colored flowers, and a great number of inflorescences.

Duege was originated from a hybridization made in a controlled breeding program in Rheinberg, FRG, in 1984. The female parent was an unnamed seedling. The male parent of Duege was an unnamed seedling.

Duege was discovered and selected as one flowering plant within the progeny of the stated cross by Guenter Duemmen in 1985 in a controlled environment in Rheinberg.

The first act of asexual reproduction of Duege was accomplished when vegetative cuttings were taken from the initial selection in July, 1985 in a controlled environment in Rheinberg by a technician working under formulations established and supervised by Guenter Duemmen. Horticultural examination of selected units initiated in October, 1985 has demonstrated that the combination of characteristics as herein disclosed for Duege are firmly fixed and are retained through successive generations of asexual reproduction.

Duege has not been observed under all possible environmental conditions. The phenotype may vary significantly with variations in environment such as temperature, light intensity, and day length. The following observations, measurements, and comparisons describe plants grown in Rheinberg under greenhouse conditions which approximate those generally used in commercial practice.

The following traits have been repeatedly observed and are determined to be basic characteristics of Duege which in combination distinguish this geranium as a new and distinct cultivar:

1. New kind of color;
2. Great number of umbels;
3. Semi double flower form;
4. Very early time of beginning of flowering;

Of the many commercial cultivars known to the present inventor(s), the most similar in comparison to Duege is Casino (Floranova). Reference is made to attached Chart A which compares certain characteristics of Duege to those same characteristics of Casino. In comparison to Casino, Duege has greater number of umbels, earlier time of beginning of flowering, and no white color on the lower side of the lower petals.

The accompanying photographic drawing(s) show typical flower and foliage characteristics of Duege, with colors being as true as possible with illustrations of this type.

In the following description color references are made to The Royal Horticultural Society Colour Chart. The color values were determined between 10:00–2:00 p.m. on Feb. 10, 1988 under natural light conditions at Rheinberg.

Classification:

*Botanical.*—*Pelargonium zonale* cv. Duege.

*Commercial.*—Geranium.

INFLORESCENCE

A. Umbel:

*Average diameter.*—9 to 11 cm.

*Average depth.*—7 to 8 cm.

*Peduncle length.*—10 to 14 cm.

*Peduncle length.*—3 cm.

B. Corolla:

*Average diameter.*—3.5 to 4 cm.

*Form.*—Semi-double.

*Color (general tonality from a distance of three meters).*—RHS 46D.

*Color (abaxial).*—RHS 46D.

*Color (adaxial).*—RHS 47C.

C. Bud:

*Shape.*—Elliptic.

*Color (abaxial).*—Ca. RHS 46D.

*Color (adaxial).*—Ca. RHS 47C.

D. Reproductive organs:

*Androecium.*—Fertile, obdiplostemon, centrifugal dedouplement.

*Gynoecium.*—5-lobed stigma, pubescent, 5 carpels, coenocarp, hypogyn.

E. Spring flowering response period:

*FRG.*—50% of plants with at least one flower open 16 weeks after stick of unrooted cuttings.

F. Outdoor flower production: Continuous.

G. Durability. Good.

H. Botanical description:

*Number of florets.*—Average 7.32.

*Number of petals.*—9 to 11.

*Breadth of petals.*—1.9 cm.

*Length of petals.*—2.4 cm.

*Flower placement above leaves.*—8.0 cm.

*Flower longevity.*—3 weeks.

Propensity of the plant to set seed is only given with strong winds or insects strong engagement up to 3 per floret.

Florets have to be removed manually after end of flowering.

PLANT

A. Foliage:

*Form.*—Kidney shaped.

*Margin.*—Bicrenated, shallow.

*Color (abaxial).*—RHS 137B.

*Color (adaxial).*—RHS 138B.

*Color (zonation).*—RHS 137A.

*Tolerance of botrytis.*—Good.

B. General appearance and form:

*Internode length.*—Medium.

*Branching pattern.*—Good.

*Height.*—Medium.

C. Growing habitus:

*Height of leaves.*—27 cm.

*Length of shoots.*—9 cm.

*Diameter of plant.*—31 cm.

*Cuttings production.*—3.1 cuttings between 4th and 9th months.

Self-branching with 10.5 shoots without pinching.

The plant shown has not been treated with a growth retardant; there are no pinching requirements.

CHART A

Comparison Between DUEGE and CASINO: Comparison is based on plants 16 weeks old in 12 cm pots.

| Differences: | DUEGE | CASINO |
|---|---|---|
| Height of leaves: | 27 cm | 35 cm |
| Zoning of leaves: | Weak | Medium |
| Time of flowering: | Very early up to early | Medium up to late |
| Petal color, middle of upper petals | RHS 46D | RHS 46D |
| Petal color, middle of lower side of upper petals | RHS 47C | RHS 43C |
| Flower placement above leaves | 8 cm | 11 cm |

What is claimed is:

1. A new and distinct cultivar of Geranium known as Duege, as described and illustrated, and particularly characterized by a new color, a great number of umbels, a semi-double flower form, and very early flowering.

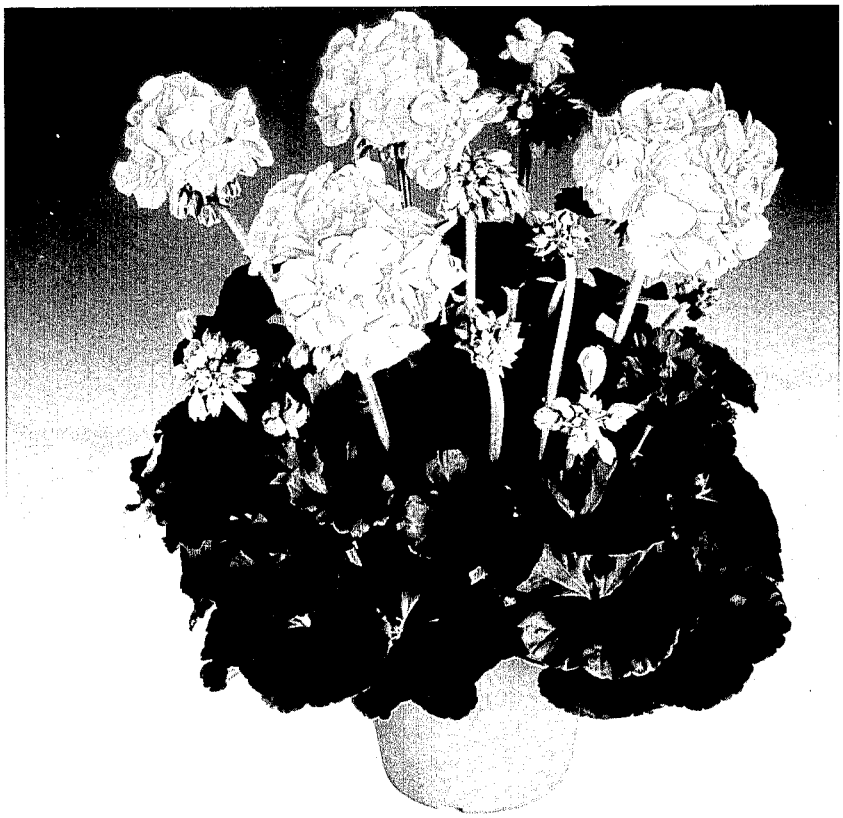

* * * * *